(12) United States Patent
Niwa et al.

(10) Patent No.: US 6,890,294 B2
(45) Date of Patent: May 10, 2005

(54) ENDOSCOPE APPARATUS

(75) Inventors: Hiroshi Niwa, Koganei (JP); Michio Sato, Hachioji (JP); Akira Taniguchi, Hachioji (JP); Fumiyuki Onoda, Tama (JP); Sumihiro Uchimura, Sagamihara (JP); Chieko Aizawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/452,085

(22) Filed: Jun. 2, 2003

(65) Prior Publication Data

US 2003/0195388 A1 Oct. 16, 2003

Related U.S. Application Data

(62) Division of application No. 10/209,199, filed on Jul. 31, 2002, now Pat. No. 6,745,065.

(30) Foreign Application Priority Data

Aug. 2, 2001 (JP) ........................................ 2001-235425
Aug. 7, 2001 (JP) ........................................ 2001-239754

(51) Int. Cl.[7] ................................................ A61B 1/00
(52) U.S. Cl. ....................... 600/106; 600/104; 600/153; 600/154
(58) Field of Search ............................... 600/104, 106, 600/153, 154

(56) References Cited

U.S. PATENT DOCUMENTS

| | | | | |
|---|---|---|---|---|
| 4,240,411 A | * | 12/1980 | Hosono | ...................... 600/154 |
| 4,920,953 A | * | 5/1990 | McGown | ...................... 600/154 |
| 6,165,124 A | * | 12/2000 | Ouchi | .......................... 600/154 |
| 6,254,529 B1 | * | 7/2001 | Ouchi | .......................... 600/154 |
| 2004/0006356 A1 | * | 1/2004 | Smith | .......................... 606/167 |

FOREIGN PATENT DOCUMENTS

| | | |
|---|---|---|
| JP | 9-103433 | 4/1997 |
| JP | 10-75929 | 3/1998 |

* cited by examiner

*Primary Examiner*—Beverly M. Flanagan
(74) *Attorney, Agent, or Firm*—Scully, Scott, Murphy & Presser

(57) ABSTRACT

An endoscope apparatus comprises an endoscope having a treatment tool passage channel in at least an insertion portion, an adaptor for endoscope forceps opening, which can be detachably attached to a treatment tool insertion opening which is at one end of the treatment tool passage channel, an insertion shape detection probe provided with a plurality of shape detection elements which are to be passed and arranged in the treatment tool passage channel via the adaptor for endoscope forceps opening, an insertion shape detection unit for detecting magnetic field emitted from the shape detection elements of the insertion shape detection probe, an insertion shape detection device which drives the insertion shape detection probe and outputs video signals for visualizing the insertion shape from the signals corresponding to the magnetic field detected by the insertion shape detection unit, and a display device for displaying the insertion shape of the insertion portion based on the video signals output from the insertion shape detection device.

5 Claims, 13 Drawing Sheets

ENDOSCOPE APPARATUS

CROSS REFEERENCE TO RELATED APPLICATION

This application is a divisional application of U.S. Ser. No. 10/209,199 filed on Jul. 31, 2002, now U.S. Pat. No. 6,745,065, the entire contents of which is incorporated herein by its reference.

This application claims benefit of Japanese Applications No. 2001-235425 filed on Aug. 2, 2001, and No. 2001-239754 filed on Aug. 7, 2001, the contents of which are incorporated by this reference.

BACKGROUND OF THE INVENTION

1. Field of the Invention

The present invention relates to an endoscope apparatus in which the shape of endoscope insertion portion can be confirmed.

2. Description of the Related Art

Endoscopes have recently come into wide use in the fields of medical treatment and industry. In endoscopes with a flexible insertion portion, this insertion portion can be inserted into curved body cavities. Inserting the insertion portion into a body cavity makes it possible to conduct diagnostics of organs on the deep part of the body cavity, without surgery, or to conduct, if necessary, the treatment such as removal of polyps by passing a treatment tool through a passage channel of the endoscope.

However, when examination inside the colon is conducted by passing an endoscope with an elongated endoscope, for example, through the anus, certain skills are required for smoothly inserting the insertion portion into the curved body cavity. This is because, the shape of the inserted portion of the endoscope, for example, the distal end of the endoscope inside the body cavity, cannot be determined.

In order to make it possible to determine the shape of the inserted portion of the endoscope, a section which is not transparent to X rays can be provided on the insertion portion, this section allowing the insertion shape of the endoscope to be grasped by irradiating X ray. In other words, the detection of the distal end position or curved shape of the insertion portion inside a body cavity can be detected by irradiating the body with X rays.

However, endoscope shape detectors using X rays have a large size, and sufficiently large examination rooms are required to accommodate such devices. Furthermore, during endoscopic examination, the operator has to conduct the operation of X ray irradiation in addition to the endoscope operation. As a result, the burden on the operator is increased. Furthermore, frequent irradiation with X rays increases the radiation dose and can be dangerous for both the patient and the operator. With the foregoing in view, detecting the shape of the insertion portion of the endoscope by using X rays is not necessarily the desirable method.

For this reason, an insertion portion shape detection device has been suggested in which an insertion shape detection probe provided, for example, with a plurality of magnetic field detection elements, and a magnetic field detector are used, the insertion shape detection probe is passed into and arranged in a passage channel provided in the endoscope, signals from the magnetic field detection elements are received by the detection device arranged outside, and the shape of the inserted portion of the endoscope is displayed on the screen of the detection device.

However, in order to detect accurately the shape of the insertion portion by passing and arranging the insertion shape detection probe in the treatment tool passage channel, a small-diameter insertion shape detection probe has to be formed and a plurality of elements and signal lines extending from those elements have to be arranged in the insertion shape detection probe.

In the conventional process for forming the insertion shape detection probe, a plurality of elements and signal lines are arranged inside a tube and then the inside of the tube is filled, for example, with silicon as a solvent. Accordingly, the manufacturing process is difficult and time consuming. Moreover, unfavorable effects such as nonuniform arrangement of signal lines during filling with the solvent could be a problem.

When a shape detection probe with desired specifications could not be manufactured because of nonuniform arrangement of signal lines and a curving or twisting operation is conducted with such an insertion shape detection probe arranged in the treatment tool passage channel, the signal lines located inside the tube could be stretched and ruptured.

Furthermore, the insertion shape detection probe is not fixed with respect to the treatment tool passage channel. As a result, movement of the insertion shape detection probe inside the treatment tool passage channel could make impossible the accurate detection of the insertion portion shape. Moreover, when the operation of twisting the insertion portion or bending the curved section is conducted, there is a risk of the insertion shape detection probe protruding from the distal end surface of the endoscope. Accordingly, the insertion procedure is implemented by moving the distal end of the insertion shape detection probe to the operating end by a prescribed distance from the prescribed position inside the treatment tool passage channel and preventing the protrusion thereof. For this reason, too, there is a possibility that accurate detection of the insertion portion shape could not be conducted.

SUMMARY OF THE INVENTION

It is an object of the present invention to provide an endoscope apparatus in which the detection of the insertion portion shape can be conducted with a high accuracy by passing and arranging an insertion shape detection probe in the treatment tool passage channel.

Another object of the present invention is to provide an insertion shape detection probe that has excellent assembling ability and durability.

It is yet another object of the present invention to provide an adaptor for an endoscope forceps opening by which positioning of the treatment tool passed into the treatment tool passage channel can be reliably conducted and, if necessary, changing of the treatment tool position can be conducted in a stepwise manner.

The endoscope apparatus in accordance with the present invention comprises an endoscope having a treatment tool passage channel in at least an insertion portion, an adaptor for endoscope forceps opening, which can be detachably attached to a treatment tool insertion opening at one end of the treatment tool passage channel, an insertion shape detection probe provided with a plurality of shape detection elements which are to be passed through and arranged in the treatment tool passage channel via the adaptor for endoscope forceps opening, an insertion shape detection unit for detecting magnetic field emitted from the shape detection elements of the insertion shape detection probe, an insertion shape detection device which drives the insertion shape detection probe and outputs video signals for visualizing the insertion shape based on the signals corresponding to the magnetic field detected by the insertion shape detection unit, and a display device for displaying the insertion shape of the insertion portion based on the video signals output from the insertion shape detection device. Therefore, detection of the insertion portion shape can be conducted with a high accuracy by passing the insertion shape detection probe into the treatment tool passage channel.

The above and other object, features and advantages of the invention will become more clearly understood from the following description referring to the accompanying drawings.

DESCRIPTION OF THE PREFERRED EMBODIMENTS

Figure 1:
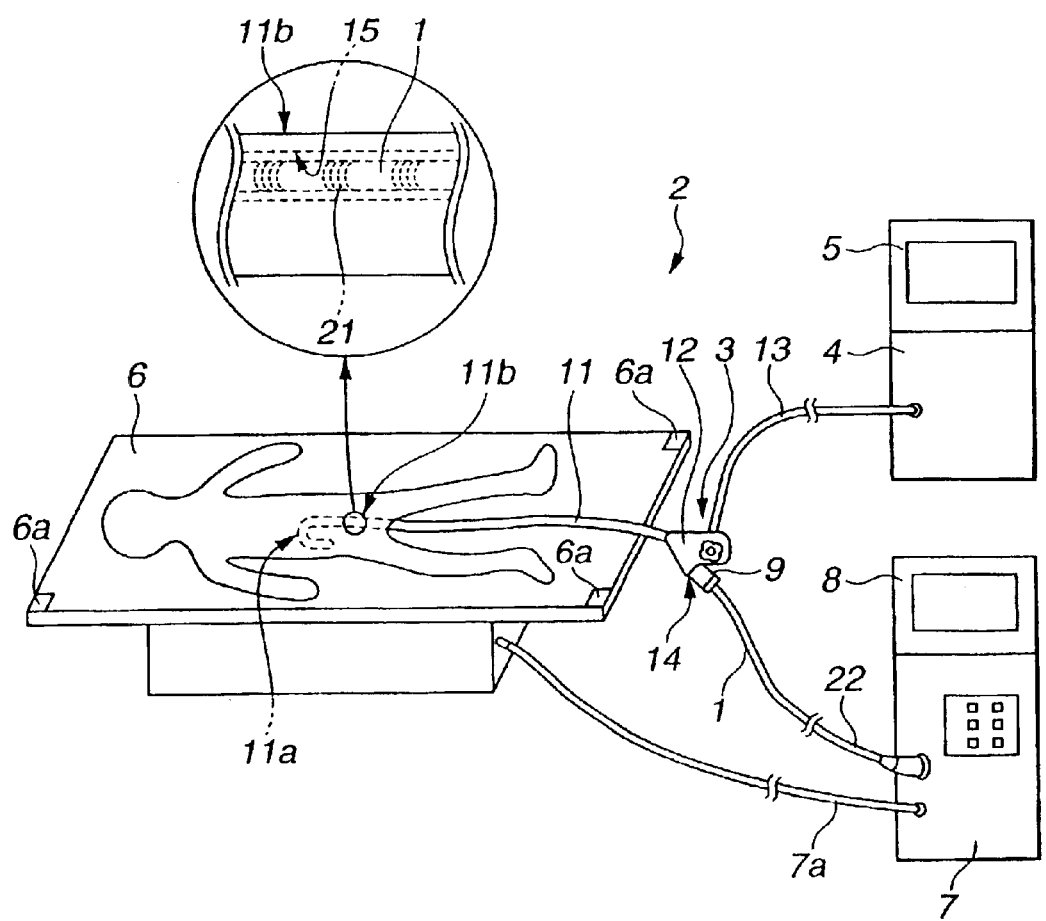
FIG. 1 illustrates an insertion portion shape detection device.

As shown in FIG. 1, the endoscope apparatus 2 using an insertion shape detection probe 1 of the present embodiment is composed mainly of an endoscope 3, a video processor 4, a monitor 5 which is a display device, a bed 6 for insertion shape detection, an insertion shape detection device 7, a monitor 8 which is a display device, and an adaptor 9 for endoscope forceps (referred to hereinbelow as adaptor).

The endoscope 3 comprises an image pickup element (not shown in the figures) and is inserted into a body cavity of a patient, for example, through the anus for observing an observation zone. The video sensor 4 generates a video signal from the image pickup signal transmitted by the endoscope 3 that has picked up the image. The motor 5 receives the image signal output from the video processor 4 and displays the insertion portion shape image. The patient lies on the bed 6 for insertion shape detection and the bed senses the magnetic field from the insertion shape detection probe 1. The insertion shape detection device 7 drives the insertion shape detection probe 1 and outputs a video signal that visualizes the insertion shape of the endoscope 3 inside the body cavity from the signal corresponding to the magnetic field detected by the bed 6 for insertion shape detection. The monitor 8 displays the insertion portion shape that was output from the insertion shape detection device 7. The adaptor 9 is mounted on the below-described treatment tool insertion opening denoted by the reference symbol 14 and allows an operation of attaching the treatment tool in the prescribed state and an operation of changing stepwise the position of the treatment tool to be performed.

The endoscope 3 comprises an insertion portion 11, an operation unit 12 serving also as a gripping portion, and a universal cord 13 connected to an external device such as the video processor 4 or the like. The insertion portion 11 has a thin elongated shape allowing the portion to be inserted into a body cavity. The operation unit 12 is connected to the proximal end side of the insertion portion 11. The universal cord 13 extends from the side part of the operation unit 12.

The insertion shape detection probe 1 is inserted into and arranged inside a treatment tool passage channel 15 via the adaptor 9 arranged in the treatment tool insertion opening 14 provided in the operation unit 12 of the endoscope 3. For example, a plurality of source coils 21, which are magnetic field generation elements that generate magnetic field, are arranged as shape detection elements in the insertion shape detection probe 1. The insertion shape detection probe 1 is connected to the insertion shape detection device 7 via the connector portion 22.

On the other hand, a plurality of sensor coils 6a, which are the magnetic field sensing elements representing the insertion shape detection portions that sense the magnetic filed generated by the source coils 21, are arranged in the bed 6 for insertion shape detection. The bed 6 for insertion shape detection and insertion shape detection device 7 are connected with a cable 7a. Therefore, signals sensed by the sensor coils 6a are transmitted to the insertion shape detection device 7 via the cable 7a.

The insertion shape detection device 7 comprises a source coil drive unit (not shown in the figure) for driving the source coils 21, a source coil position analysis unit (not shown in the figure) for analyzing the three-dimensional position coordinates of the source coils 21 from the signals transmitted by the sensor coils 6a, an insertion shape image generation unit (not shown in the figures) for calculating the three-dimensional shape of the insertion portion 11 from the three-dimensional position coordinate information of the source coils 21, converting them into two-dimensional coordinates for monitor display, and visualizing.

The structure of the insertion shape detection probe 1 will be described hereinbelow in greater detail with reference to FIGS. 2 to 9.

Figure 2:
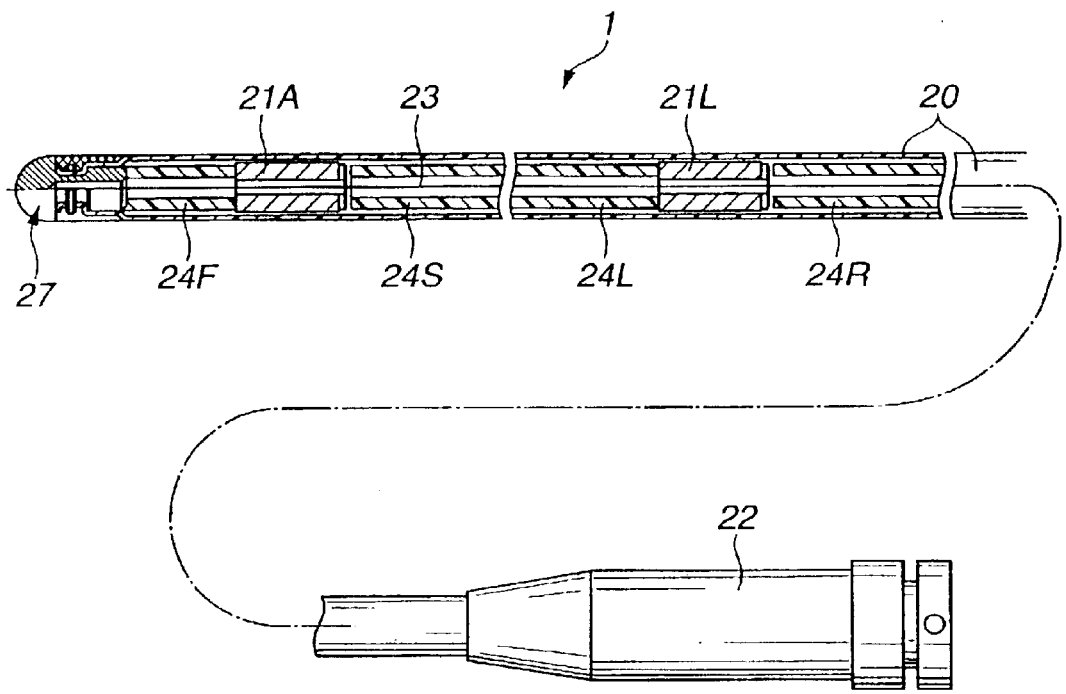
FIG. 2 illustrates an insertion shape detection probe.
Figure 3A:
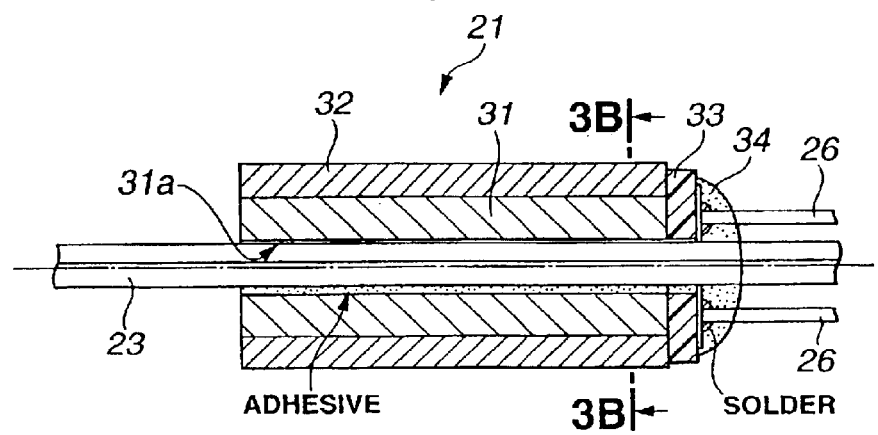
FIG. 3A is a sectional view illustrating the structure of source coils and core wire.
Figure 3B:
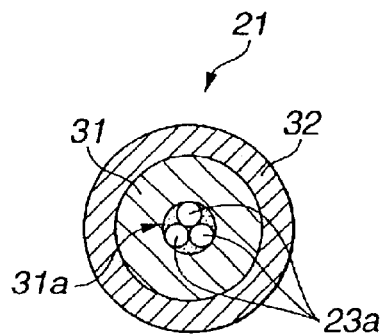
FIG. 3B is a sectional view along the 3B—3B line in FIG. 3A.

As shown in FIGS. 2 to 3B, the insertion shape detection probe 1 is mainly composed of an outer sheath 20, a plurality of source coils 21A, . . . , 21L, a thin long core wire 23, and tubular inner sheaths 24. The outer sheath 20 is to be passed inside the treatment tool passage channel 15 constituting a sheathing. The plurality of source coils 21A, . . . 21L are hollow. The core wire 23 is adhesively fixed to the source coils 21A, . . . , 21L. The inner sheaths 24 are arranged in series with respective source coils 21A, . . . , 21L. In other words, the source coils 21A, . . . , 21L and inner sheaths 24 are arranged alternately in series in the order of source coil 21A, inner sheath 24, source coil 21B, . . . .

Further, the insertion shape detection probe 1 of the present embodiment, for example, comprises twelve source coils. The source coil at the distal end will be referred to as a first source coil 21A, followed by the second source coil 21B, . . . , twelfth source coil 21L.

Furthermore, signal lines 26 for transmitting drive signals are connected to one end of source coils 21A, . . . , 21L. Accordingly, signal lines extending from the source coils 21A, . . . , 21L will be referred to as signal lines 26A, . . . , 26L. The reference numeral 27 denotes a distal end piece disposed at the distal end of outer sheath 20.

In the present embodiment, the outer coating of the outer sheath 20, inner sheaths 24, and signal lines 26 is made of Teflon (registered trade name). Teflon (registered trade name) cannot be fixed with an adhesive and this specific property thereof is used herein. When fixing with an adhesive is conducted, the bonding surface is roughened by pretreatment and tetraetching is conducted so that the adhesive can stick thereto.

As shown in FIG. 3A, the source coil 21 is composed of a hollow core member 31 having an axial through hole 31a, a winding 32 wound on the core member 31, and a core substrate 33 shaped almost as a donut and provided on an end surface side of the core member 31. The source coils 21 are fixed to the core wire 23 in the prescribed positions with an adhesive. The winding 32 is electrically connected to the core substrate 33, and the signal line 26 is electrically connected thereto, for example, with a solder. Further, the reference numeral 34 stands for an adhesive agent layer protecting the substrate pattern surface containing the solder.

As shown in FIG. 3B, the core wire 23 disposed inside the axial through hole 31a is composed of three linear shape memory alloy wires 23a arranged parallel each other. The diameter of the circumscribed circle formed by the three linear shape memory alloy wires 23a constituting the core wire 23 is made almost equal to the inner diameter of the axial through opening 31a. Strictly speaking, the circumscribed circle has a somewhat smaller diameter than the inner diameter of axial through opening 31a.

As a result, because the source coils 21 are passed through the core wire 23, the core member 31 assumes a position in which it is supported in three points by the shape memory alloy wires 23a and shaking can be prevented. Moreover, the axial line of core wire 23 and the axial line of the source coils 21 can be maintained in a parallel positional relationship. With an adhesive coated in such an attached state, the source coils 21 are reliably bonded and fixed to the core wire 23 in the prescribed state. Therefore, assembling ability is improved.

Figure 4:
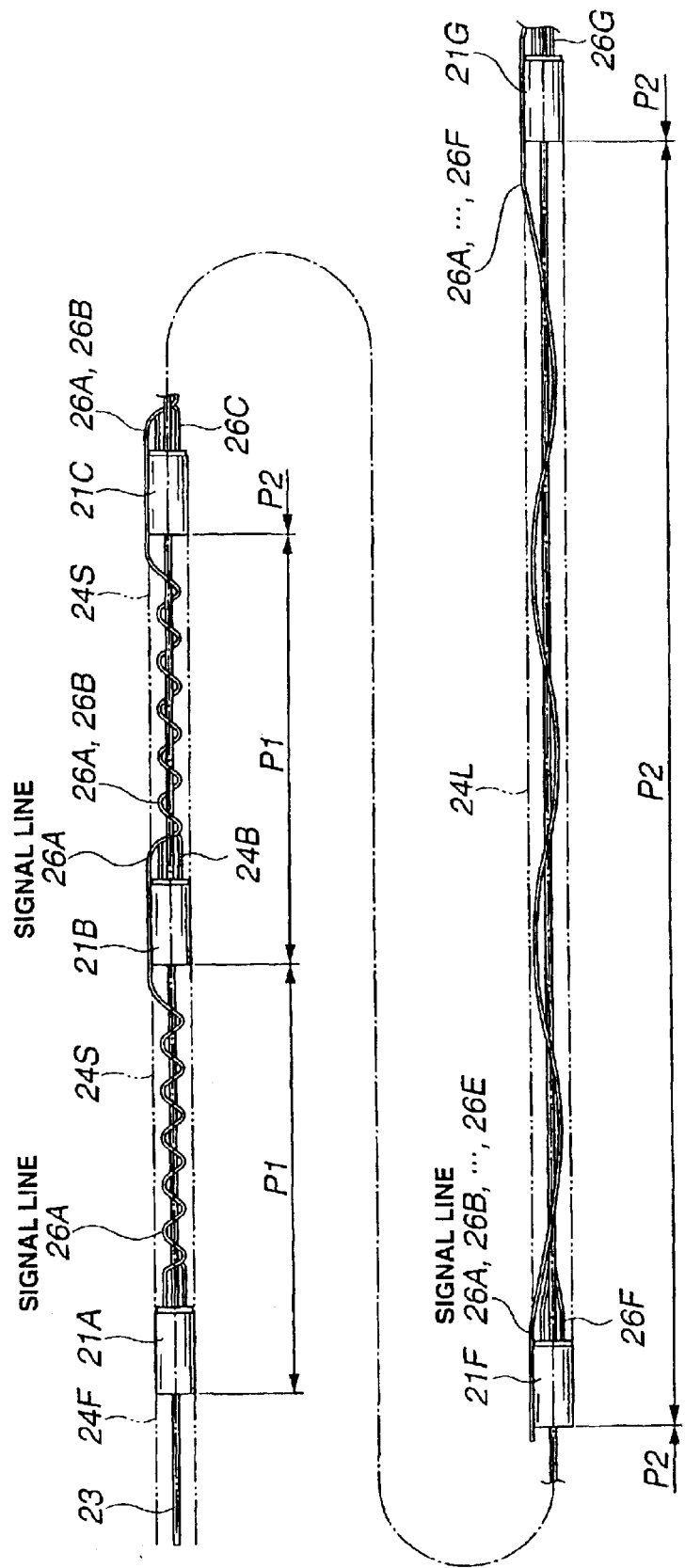
FIG. 4 illustrates the arrangement positions of source coils that are arranged inside the outer sheath and the winding state of signal lines wound along the core wire.

As shown in FIG. 4, in the source coils 21A, . . . , 21L fixed to the core wire 23, spacing between the elements differs depending on the zone in which they are arranged. The source coils 21A, 21B, 21C constitute a group of curved section shape detection elements for obtaining shape data on an insertion portion curved section 11a and are disposed in the insertion portion curved section 11a which is curved at a small curvature radius (see FIG. 1). The source coils 21D, . . . , 21L constitute a group of flexible tube section shape detection elements for obtaining shape data on an insertion portion flexible tube section 11b and are disposed in the insertion portion flexible tube section 11b which is curved at a comparatively large curvature radius (see FIG. 1). More specifically, a pitch (denoted as P1 in the figure) between the source coils 21A, 21B, 21C is set, for example, for 30 mm, and a pitch (denoted as P2 in the figure) between the source coils 21D, . . . , 21L is set, for example, for 100 mm.

As a result, the inner sheath 24 arranged in series at the proximal end sides of the source coils 21A, 21B will be referred to as an inner sheath 24S corresponding to a pitch of 30 mm. Further, the inner sheath 24 arranged in series at the proximal end sides of source coils 21D, . . . , 21K will be referred to as an inner sheath 24L corresponding to a pitch of 100 mm. The inner sheath 24 arranged in series at the proximal end side of source coil 21L and also acting to provide firmness to the proximal end side of the outer sheath 20 will be referred to as an inner sheath 24R (see FIG. 2). The inner sheath 24 arranged in series at the distal end side of the source coil 21A and also acting to provide firmness to the distal end side of the outer sheath 20 will be referred to as an inner sheath 24F (see FIG. 2).

Figure 5A:
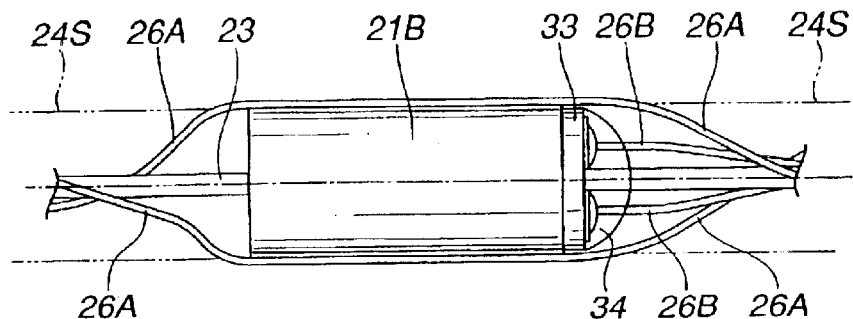
FIG. 5A illustrates signal lines passing through the source coil at the distal end side and signal lines extending from this source coil.
Figure 5B:
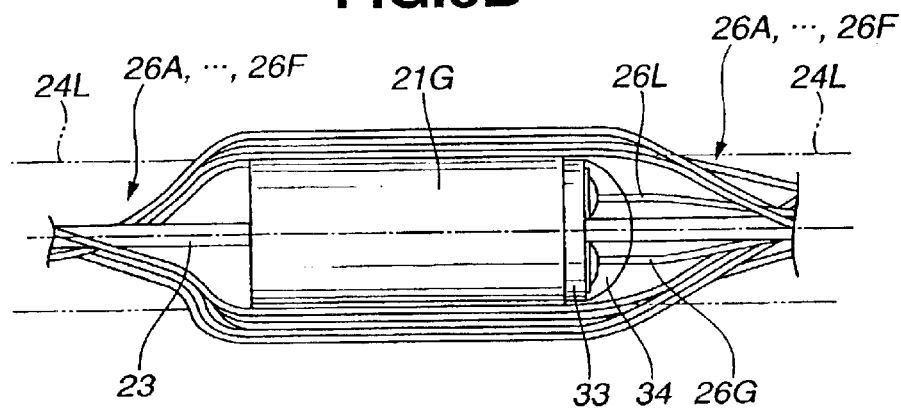
FIG. 5B illustrates signal lines passing through the source coil positioned in the intermediate portion and signal lines extending from this source coil.

As shown in FIG. 4 to FIG. 5B, signal lines 26A, . . . , 26L connected to respective source coils 21A, . . . , 21L pass inside the inner sheaths 24S, 24L, 24R arranged at the proximal end portions of respective source coils 21A, . . . , 21L and extend to the proximal end side. Signal lines 26A, . . . , 26K that pass through the inner sheaths 24S, 24L and are led out from the proximal end side are again led into the inner sheaths 24S, 24L, 24R through the side peripheral surface of source coils 21B, . . . , 21L and extend to the proximal end side. Therefore, a large number of signal lines pass inside the inner sheaths 24L, 24R positioned on the proximal end side.

Those signal lines 26A, . . . , 26L passing inside the inner sheaths 24S, 24L, 24R are coiled with the prescribed looseness along the core wire 23. This is done to prevent the signal lines 26A, . . . , 26L from being stretched and ruptured when the insertion shape detection probe 1 is bent.

More specifically, signal lines 26A, 26B wound among the source coils 21A, 21B, 21C arranged in the insertion portion curved section 11a which is curved at a small curvature radius are wound 5–6 times with a sufficient looseness on the core wire 23. By contrast, signal lines 26A, . . . , 26L wound between the source coils 21D, . . . , 21L arranged in the insertion portion flexible tube section 11b which is bent at a comparatively large curvature radius are wound 2–3 times with a certain looseness on the core wire 23.

Figure 6A:
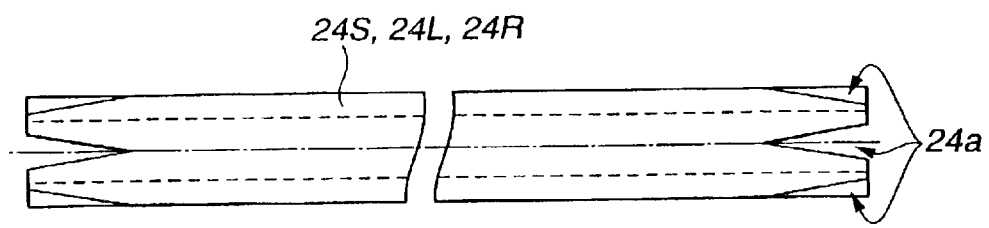
FIG. 6A illustrates split grooves formed in the end portions of inner sheaths.

As shown in FIG. 6, from 2 to 4 slit grooves 24a are formed in the end portions of the inner sheaths 24S, 24L, 24R so as to prevent a plurality of signal lines 26 from being arranged on one side only and also to prevent the signal lines 26 led into (or led out from) the inner sheaths 24S, 24L, 24R from being bent sharply.

Figure 7A:
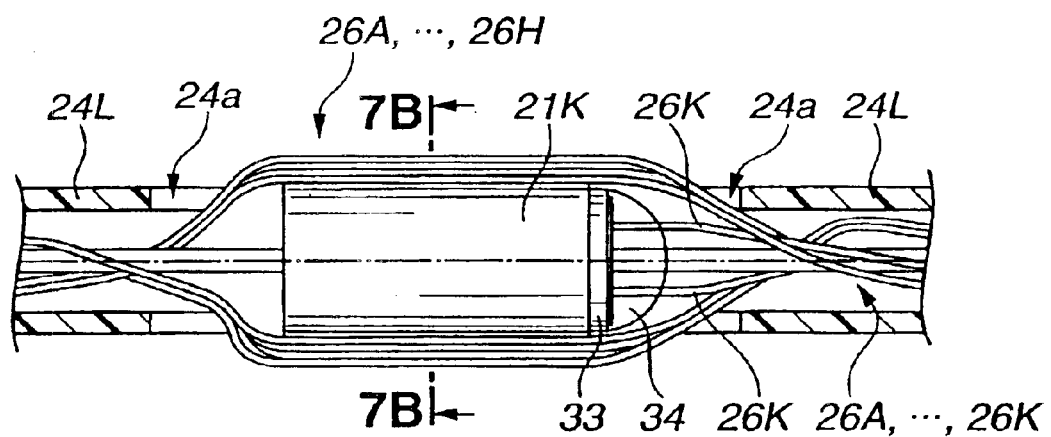
FIG. 7A illustrates action of slit grooves in the longitudinal axial direction.

Therefore, as shown in FIG. 7A, when signal lines 26A, . . . , 26H are led out from the inside of the inner sheath 24L, which is positioned at a distal end side, for example, toward the source coil 21K of the group of flexible tube section shape detection elements, those signal lines 26A, . . . , 26H are led out from respective slit grooves 24a toward the side peripheral surface of source coil 21K. As a result, the angle of the signal lines 26A, . . . , 26H, which are being led out, with respect to the axial direction is obtuse.

Further, when the signal lines 26A, . . . , 26H that have been passed through the side peripheral surface of source coil 21K are again led into the inner sheath 24L positioned at the proximal end side, the signal lines 26A, . . . , 26H are led in from the inner side surface of the source coil 21K toward the slit groove 24a. As a result, the angle of the signal lines 26A, . . . , 26H, which are being led in, with respect to the axial direction is obtuse.

Figure 7B:
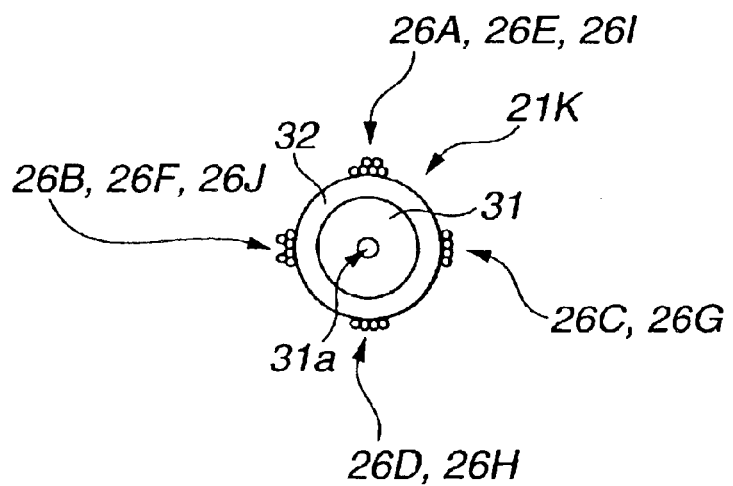
FIG. 7B is a sectional view along the 7B—7B line in FIG. 7A.

On the other hand, by leading the plurality of signal lines 26A, . . . , 26H, which pass inside the inner sheath 24L, dispersedly from the prescribed slit groove 24a to the source coil 21K, it is possible to disperse the signal lines 26A, . . . , 26H uniformly with respect to the side peripheral surface of the source coil 21K, as shown in FIG. 7B.

As a result of the above-described features, the signal lines can be dispersedly arranged in a uniform manner on the side peripheral surface of source coils and the diameter of the signal lines can be shortened. Moreover, breakage of signal lines caused by rapid rising thereof in the vicinity of the end surface of source coil can be prevented and endurance of the signal lines can be improved.

Figure 6B:
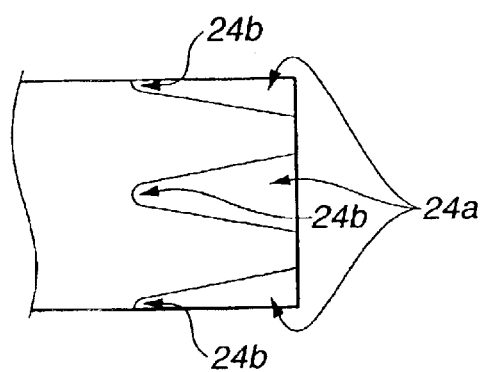
FIG. 6B illustrates another configuration example of split grooves.

Further, providing curved surface portions 24b at the bottom of the slit grooves 24a, as shown in FIG. 6B, makes it possible to prevent the outer layer, which is the cover of signal lines 26 that are led out (or led in) from the slit grooves 24a, from being damaged at the edge of the slit grooves 24a.

Figure 8:
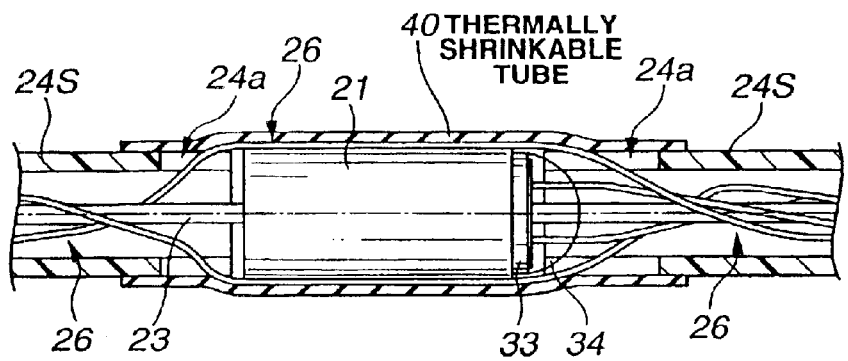
FIG. 8 illustrates a state in which the gap between the source coil and inner sheath is covered with a thermally shrinkable tube.

As shown in FIG. 8, an integrated structure is obtained with a thin-wall thermally shrinkable tube 40 which coats the source coil 21 and inner sheath 24S and to eliminate gaps between the source coils 21 and inner sheath 24S. More specifically, the thermally shrinkable tube 40 covers the side peripheral surface of the source coils 21 where the signal lines 26 are arranged, those source coils constituting a group of curved section shape detection elements, and also covers the end portion of the inner sheath 24S where the slit grooves 24a are formed, through which the signal lines 26 are led out, and the end portion of the inner sheath 24 where the slit grooves 24a are formed through which the signal lines 26 are led in.

The source coils and signal lines arranged on the side peripheral surface of the source coils are thus integrated and fixed. Moreover, the signal lines led out or led in from the slit grooves are prevented from being exposed, and contact between the signal lines and outer sheath during assembly or usage is also prevented. Thus, endurance during assembly or usage can be improved.

Further, since the integrated structure is obtained by covering the source coils and the inner sheaths adjacent thereto with a thermally shrinkable tube, the shrinking action of the thermally shrinkable tube produces an effect of a fracture-arresting member, and buckling in the joint zone of the source coils and inner sheaths can be avoided. Moreover, forming a parallel configuration in the longitudinal axial direction can improve assembling ability.

Figure 9A:
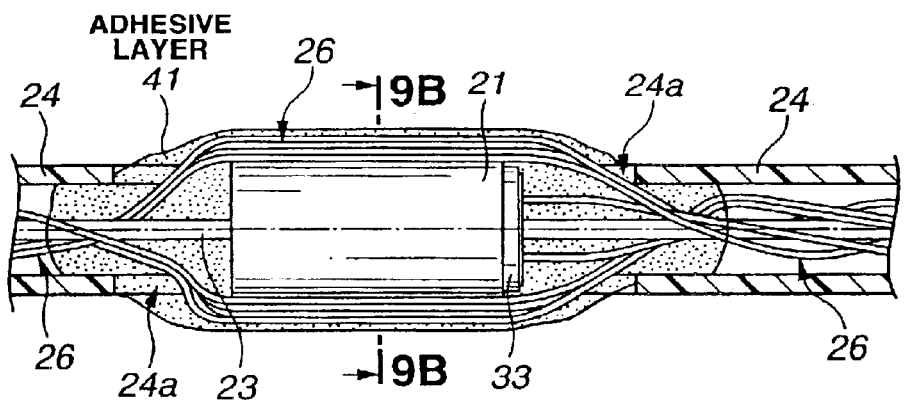
FIG. 9A illustrates the adhesive layer in the longitudinal axial direction.
Figure 9B:
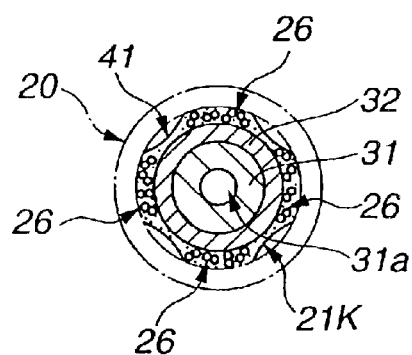
FIG. 9B is a sectional view along the 9B—9B line in FIG. 9A.

On the other hand, FIG. 9A and FIG. 9B show an integrated structure obtained by providing an adhesive layer 41 to eliminate the gaps between the source coils 21 and inner sheaths 24. More specifically, the adhesive layer 41 is provided to coat the side peripheral surface of source coils 21 where the signal lines 26 are arranged, those source coils constituting a group of flexible tube section shape detection elements, and also covers the end portions of the inner sheaths 24 where the slit grooves 24a are formed, through which the signal lines 26 are led out, and the end portion, of the inner sheath 24, where the slit grooves 24a are formed through which the signal lines 26 are led in.

The source coils and signal lines arranged on the side peripheral surface of the source coils are thus integrated and fixed. Moreover, the signal lines led out or led in from the slit grooves are prevented from being exposed, and contact between the signal lines and outer sheath during assembly or usage is also prevented.

Further, obtaining the integrated structure of a source coil and an inner sheath adjacent thereto makes it possible to avoid buckling in the joint zone of the source coil and inner sheath.

The above-mentioned tetraetching treatment, which is a pretreatment, is conducted when an adhesive layer 41 is provided. At this time, the treatment is conducted by setting a certain distance from the end surface of the inner sheath so as to prevent the hard portion of the adhesive layer 41 from growing longer due to excess build-up of the adhesive. On the other hand, in order to prevent the hard portion of adhesive layer 41 from getting bigger, after the adhesive coating has been completed, a thermally shrinkable tube is put on and thermally shrunk, thereby removing the excess adhesive and forming a thin adhesive layer 41 on the source coils 21. As a result, a parallel configuration in the longitudinal axial direction is obtained and assembling ability can be improved. Furthermore, a ventilation channel can be provided by forming a shape such that only part of the external surface of adhesive layer 41 is brought in contact with the inner peripheral surface of the outer sheath 20.

Figure 10:
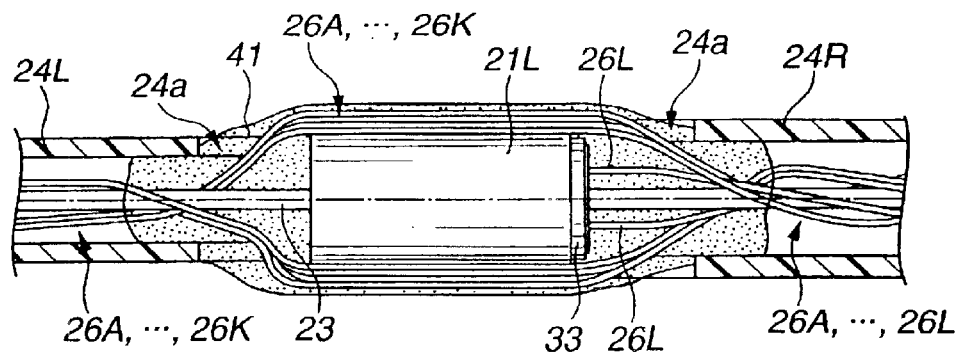
FIG. 10 illustrates a configuration example of an inner sheath arranged on the proximal end side of the source coil fixed on the proximal end side.

The number of signal lines passing through the inner sheaths increases with the increase in the number of source coils 21. Therefore, for example, as shown in FIG. 10, the assembling ability is improved by making the inner diameter of the inner sheath 24R larger than the inner diameter of the inner sheath 24L.

Figure 11:
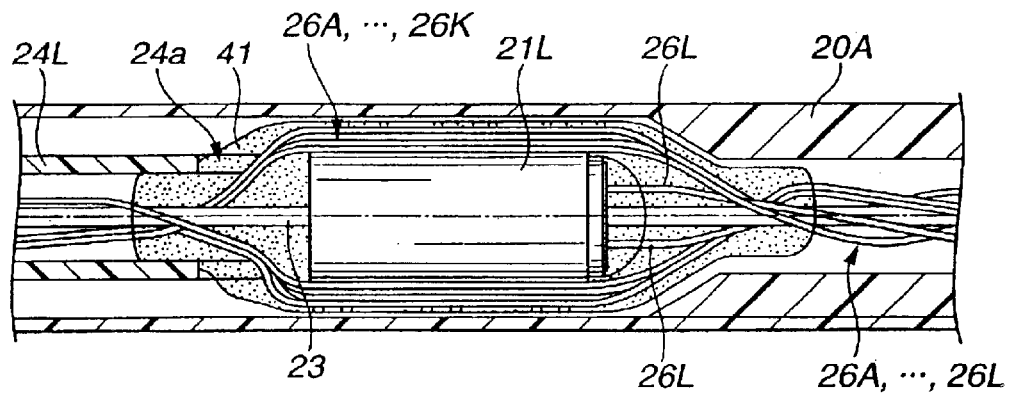
FIG. 11 is a configuration example of the outer sheath.

The assembling ability can be also improved by constructing the outer sheath 20A whose inner diameter changes in a stepwise manner, as shown in FIG. 11.

Figure 12:
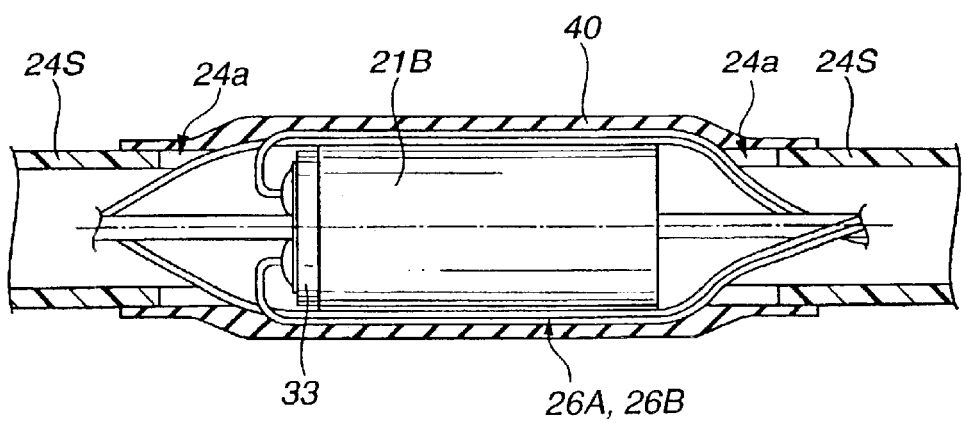
FIG. 12 illustrates another example of arrangement orientation of the source coil.

Furthermore, source coils 21B may be also integrally fixed with signal lines 26A, 26B by adhesively fixing so that the direction of the source coil 21B is reversed with respect to that of the above-described embodiment, and then coating with a thermally shrinkable tube 40, for example, as shown in FIG. 12. As a result, the number of signal lines passing through the side peripheral surface of source coils is increased, but connection portions of signal lines fixed with a solder can be loosened. As a result, contact defects in the contact portion can be reliably prevented and the endurance of contact portion can be increased.

The assembly procedure of the above-described insertion shape detection probe 1 will be briefly described below.

Step 1: a source coil 21A is passed onto the core wire 23 and adhesively fixed in the prescribed position.

Step 2: the inner sheath 24S is passed onto the core wire 23 and arranged close to the prescribed position. A signal line 26A extending from the source coil 21A is passed inside the inner sheath 24S.

Step 3: the inner sheath 24S is now moved for a while in the proximal end direction, and the signal line 26A is wound on the core wire 23.

Step 4: once winding of the signal line 26A has been completed, the inner sheath 24S is again returned to the prescribed position and tentatively fixed therein. Then, the gap between the source coil 21A and inner sheath 24S is covered with the thermally shrinkable tube 40, and an integrally fixed state is obtained. The inner sheath 24S used herein may be the one which is provided with two slit grooves 24a in the end portion thereof.

Step 5: the source coil 21B is then passed onto the core wire 23 and adhesively fixed in the prescribed position.

Step 6: the inner sheath 24S is thereafter passed onto the core wire 23 and arranged close to the prescribed position. The signal line 26A that has been led out from the slit groove 24a of the inner sheath 24S and the signal line 26B extending from the source coil 21B are passed inside the inner sheath 24S.

Step 7: the inner sheath 24S is now moved for a while in the proximal end direction, and the signal lines 26A, 26B are wound on the core wire 23.

Step 8: once winding of signal lines 26A, 26B has been completed, the inner sheath 24S is again returned to the prescribed position and tentatively fixed therein. Then, the gap between the source coil 21B and inner sheath 24S is covered with the thermally shrinkable tube 40, and an integrally fixed state is obtained.

Repeating the above-described steps produces a state in which the source coils and inner sheaths up to the source coil 21C and inner sheath 24L are integrally fixed to the core wire 23.

Step 9: the source coil 21D is then passed onto the core wire 23 and adhesively fixed in the prescribed position.

Step 10: the inner sheath 24L is thereafter passed onto the core wire 23 and arranged close to the prescribed position. The signal lines 26A, 26B, 26C that were led out from the slit groove 24a of the inner sheath 24S and the signal line 26D extending from the source coil 21D are passed inside the inner sheath 24L.

Step 11: the inner sheath 24L is now moved for a while in the proximal end direction, and the signal lines 26A, . . . , 26D are wound on the core wire 23.

Step 12: once winding of signal lines 26A, . . . , 26D has been completed, the inner sheath 24L is again returned to the prescribed position and prefixed therein. Then, the adhesive layer 41 is formed by the prescribed procedure, the gaps between the source coil 21D and inner sheaths 24S, 24L are covered, and an integrally fixed state is obtained.

Repeating the above-described steps produces a state in which the source coils and inner sheaths up to the source coil 21L and inner sheath 24R are integrally fixed to the core wire 23.

Step 13: here, a conductivity test of signal lines 26A, . . . , 26L is preformed. If normal conductivity is confirmed, the outer sheath 20 is coated. At this time, coating is completed without bringing the signal lines 26A, . . . , 26L in contact with the outer sheath 20. A distal end piece 27 is then provided at the distal end of outer sheath 20 to form a distal end side of insertion shape detection probe 1. On the other hand, the proximal end side of insertion shape detection probe 1 is formed by providing the signal lines 26A, . . . , 26L extending from the outer sheath 20 in the prescribed position of connector portion 22.

Finally, inspection is conducted as to whether the shape of insertion shape detection probe 1 is displayed on the screen of observation device. Once the inspection has been passed, final inspection as to whether pin holes have been formed in the outer sheath is conducted by injecting air from the side of connector portion 22. If the inspection is passed, the product can be shipped.

The structure of adaptor 9 will be described below in greater detail with reference to FIGS. 13 to 17.

Figure 13:
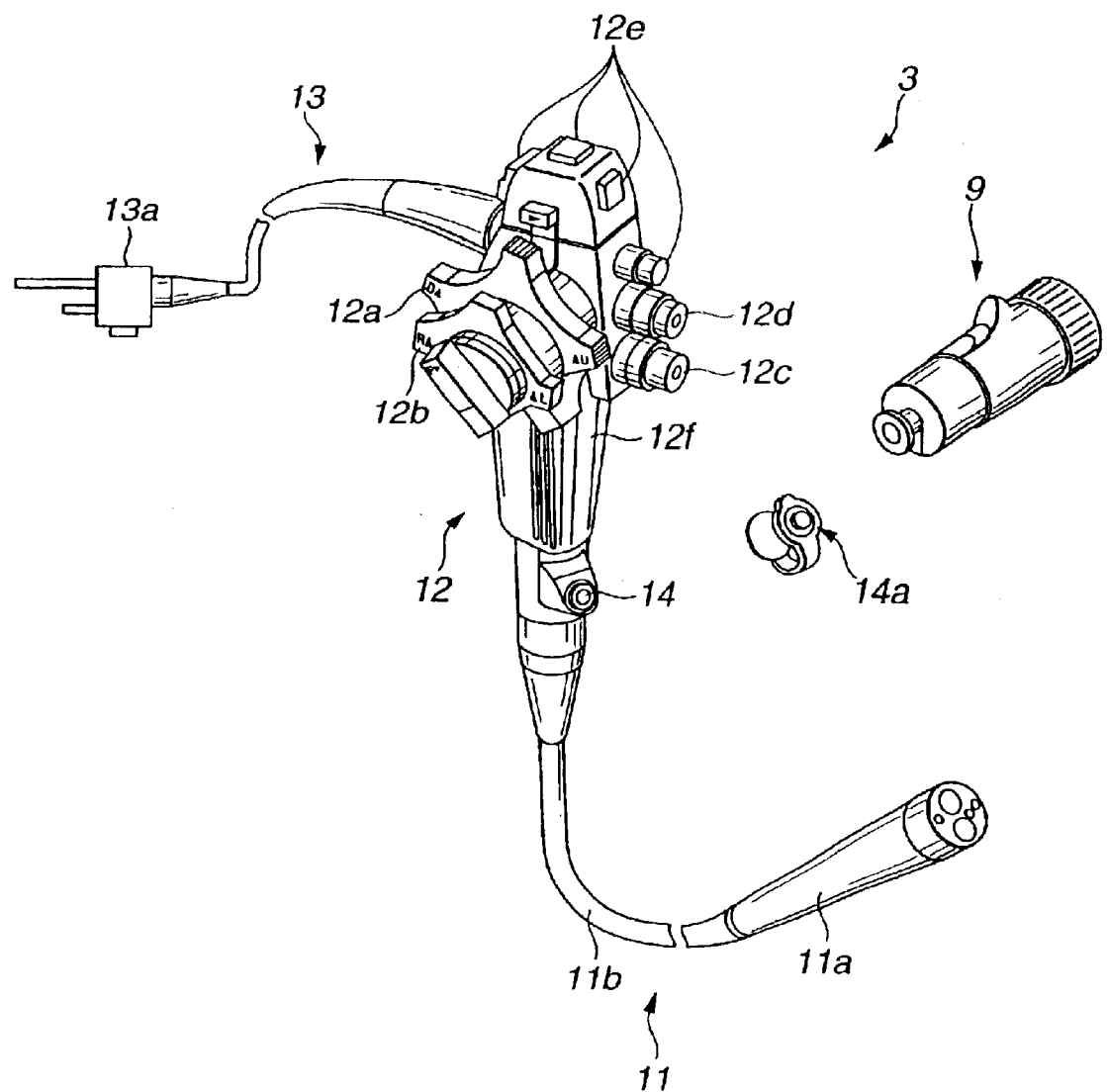
FIG. 13 illustrates the configuration of the endoscope.

As shown in FIG. 13, the operation unit 12 of the endoscope 3 of the present embodiment is provided with curved section operation knobs 12a, 12b for bending the insertion portion curved section 11a in the up-down and left-right directions, an operation button 12c for passing air and water, an operation button 12d for suction, and various control switches 12e for controlling the external devices.

A grip portion 12f formed from a hard resin material such as a polysulfone and designed for gripping is provided at the distal end side of the operation unit 12. A treatment tool insertion opening 14 for inserting the insertion shape detection probe 1 or an insertion tool such as forceps and the like is formed in the side part of the grip 12f. A forceps plug 12a formed from an elastic material such as a silicone rubber or the like is mounted on the treatment tool insertion opening 14. In the present embodiment, a configuration is employed in which the adaptor 9 is detachably mounted on the forceps plug 14a.

Figure 14:
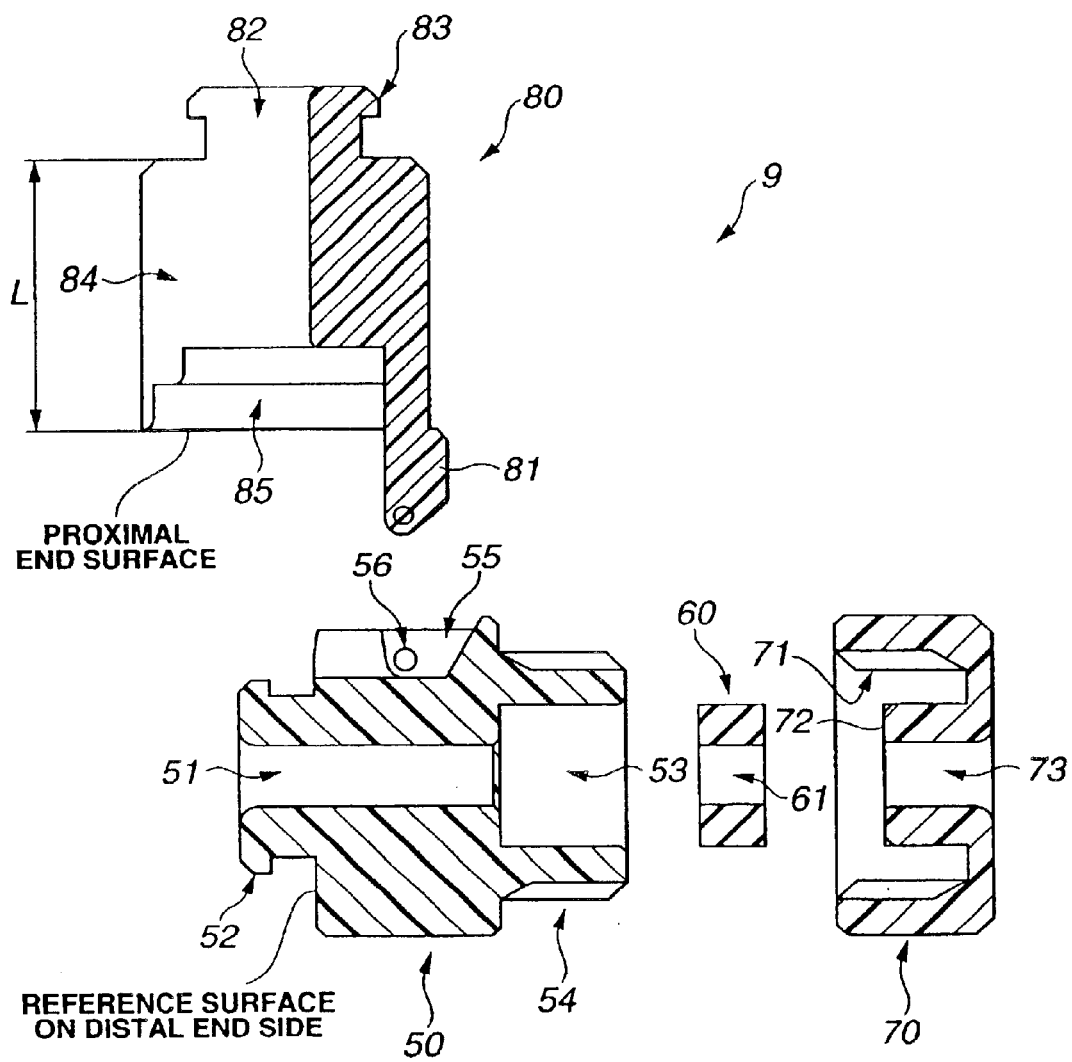
FIG. 14 illustrates structural components of the adaptor for endoscope forceps opening.

As shown in FIG. 14, the adaptor 9 is composed of an adaptor linking member 50 having a tubular shape, a treatment tool integration member 60 having a tubular shape, a pressing member 70, and a treatment tool position changing member 80 having an almost tubular shape.

The adaptor linking member 50 is formed of a resin material so that it can be detachably mounted on the forceps plug 14a. The treatment tool integration member 60 is formed of an elastic material, for example, of a rubber having elastic properties. An internal thread portion 71 for engagement with the adaptor linking member 50 is formed in the pressing member 70. The treatment tool position changing member 80 is formed of a resin material.

An adaptor through hole 51 for inserting a treatment tool is formed in the axial direction in almost the central portion of the adaptor linking member 50. A mounting protrusion 52 that can be detachably attached to the forceps plug 14a is formed at the distal end portion of the adaptor linking member 50.

Further, a recess 53 is formed in the center of the proximal end portion of adaptor linking member 50. The treatment tool integration member 60 is arranged in the recess 53. For this purpose, the inner diameter of the recess 53 is made somewhat larger than the outer diameter of treatment tool integration member 60.

Further, an external thread portion 54 for engagement with the internal thread portion 71 is formed at the side peripheral surface of the proximal end portion.

A notched portion 55 where the linking member 81 is to be arranged is formed in the prescribed position in the central portion of the side peripheral part. A mounting orifice 56 for insertion and arrangement of a pair of protrusions (not shown in the figure) provided at the linking member 81 is formed in the notched portion 55.

A through hole for fixing 61, which is to be elastically deformed and brought in intimate contact with the treatment tool, is formed in the axial direction in almost the central portion of the treatment tool integration member 60.

A pressing protrusion portion 72 formed to have the prescribed projection height dimension and designed to be brought in contact with one surface of the treatment tool integration member 60 is provided in almost the central portion of the pressing member 70. A pressing member through hole 73 for inserting the treatment tool is formed in the axial direction in almost the central portion of the pressing member 70, including the pressing protrusion 72.

A changing member through hole 82 for inserting the treatment tool is formed in the axial direction in almost the central portion of the treatment tool position changing member 80. A mounting protrusion 83 that can be detachably mounted on the forceps plug 14a is formed at the distal end portion of the treatment tool position changing member 80.

A notched portion 84 (see FIG. 16) formed so that the width dimension thereof where it is communicated with the changing member through hole 82 is almost equal to the diameter dimension of changing member through hole 82 is formed in the side peripheral surface facing the linking member 81.

A reference numeral 85 stands for an escape opening facing the mounting protrusion 52 of the adaptor linking member 50. The proximal end surface of treatment tool position changing member 80 can be brought in contact with the reference surface at the distal end side of adaptor linking member 50.

The installation of adaptor 9 will be described below.

The treatment tool integration member 60 is arranged inside the recess 53 of the adaptor linking member 50. In such an arrangement state, the internal thread portion 71 of the pressing member 70 is engaged with the external thread portion 54 of adaptor linking member 50, and the adaptor linking member 50, treatment tool integration member 60, and pressing member 70 are integrated. On the other side, the protrusion (not shown in the figures) of linking member 81 of the treatment tool position changing member 80 is introduced into the mounting orifice 56 of the adaptor linking member 50.

Figure 15:
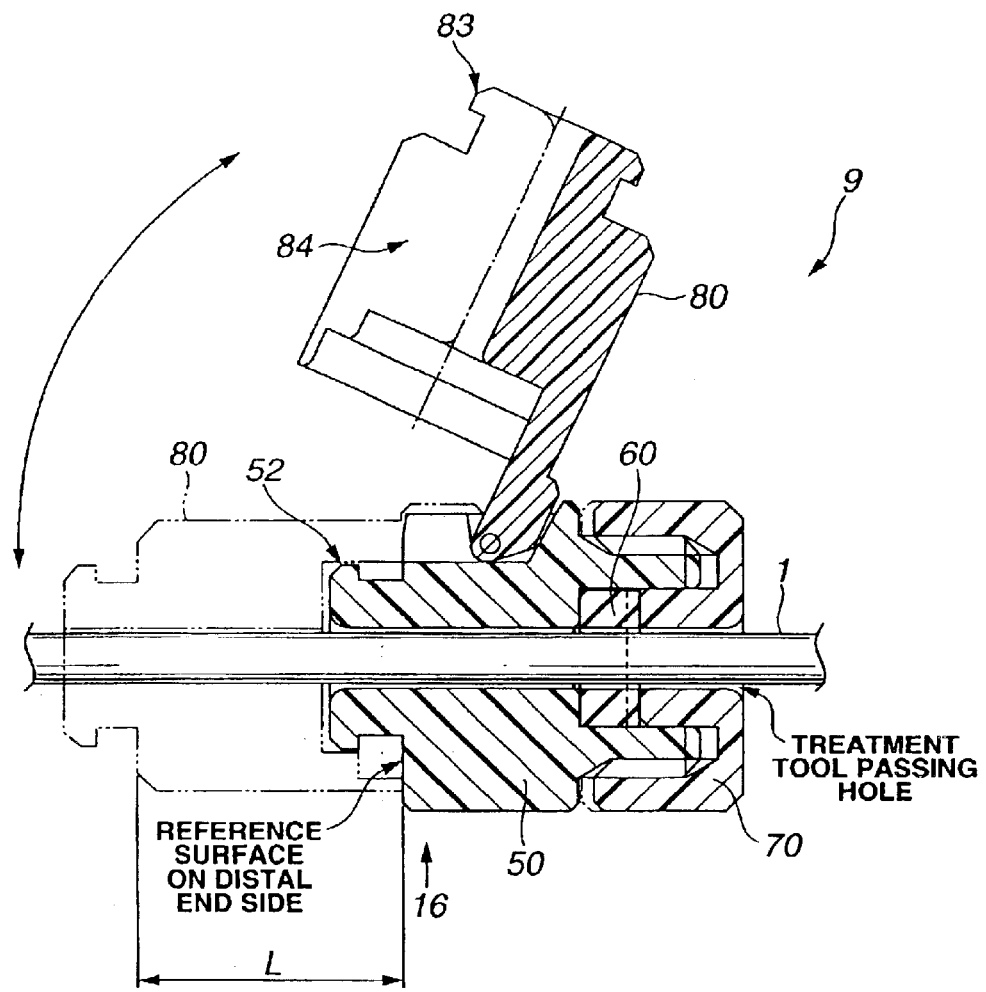
FIG. 15 illustrates the adaptor for endoscope forceps opening.

As a result, as shown in FIG. 15, the adaptor 9 is constructed such that a treatment tool insertion hole is provided for passing the treatment tool, the treatment tool position changing member 80 is free to rotate, as shown by the arrow, with respect to the adaptor linking member 50, and the length in the axial direction can be two-stepwise changed depending on whether the treatment tool position changing member 80 is disposed on the front side of the reference surface on the distal end side of-adaptor linking member 50.

Figure 16:
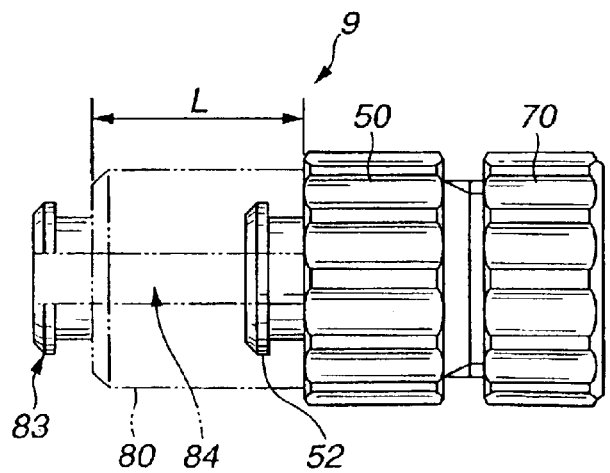
FIG. 16 is a view from the direction shown by an arrow 16 of the adaptor for endoscope forceps opening shown in FIG. 15.

In other words, because the length dimension of the treatment tool position changing member 80, which is shown by symbol "L" in FIG. 14, is set to the prescribed value, the length dimension of the adaptor 9 in the axial direction is increased by the dimension L by rotating the treatment tool position changing member 80 and arranging it in front of the reference surface on the distal end side in a state in which the mounting protrusion 52 of adaptor linking member 50 is covered with the treatment tool position changing member 80 as shown by the two-dotted chain line in FIGS. 15 and 16.

Conversely, the length dimension of the adaptor 9 in the axial direction can be decreased by the L dimension by rotating and removing the treatment tool position changing member 80 from a state in which the treatment tool position changing member 80 is arranged on the front side of the reference surface on the distal end side of adaptor linking member 50.

In the assembled state of the adaptor 9 shown in FIG. 15, the distal end surface of the pressing protrusion 72 of the pressing member 70 abuts on the end surface of the treatment tool integration member 60. In other words, the treatment tool integration member 60 is in a state before a pressing is applied by the pressing protrusion 72, and when the treatment tool is inserted in this state into the treatment tool passing hole of the adaptor 9, the treatment tool will smoothly pass inside the through hole for fixing 61 which constitutes the treatment tool passing hole.

By contrast, if the pressing member 70 is rotated and advanced to a state shown by a broken line in FIG. 15, this state being a tightened state, the pressing protrusion 72 applies pressure to the end surface of treatment tool integration member 60. As a result, the treatment tool integration member 60 is elastically deformed as shown by the broken line in FIG. 15, and the inner peripheral surface of the through hole for fixing 61 is brought in intimate contact with the periphery of the treatment tool inserted into the treatment tool passing hole of the adaptor 9.

In other words, the treatment tool integration member 60 is brought in intimate contact and fixed to the treatment tool, and a state is assumed in which the treatment tool is integrated with the adaptor 9 composed of the adaptor linking member 50, treatment tool integration member 60, and pressing member 70.

Operation of the adaptor 9 thus constructed will be described hereinbelow.

Figure 17A:
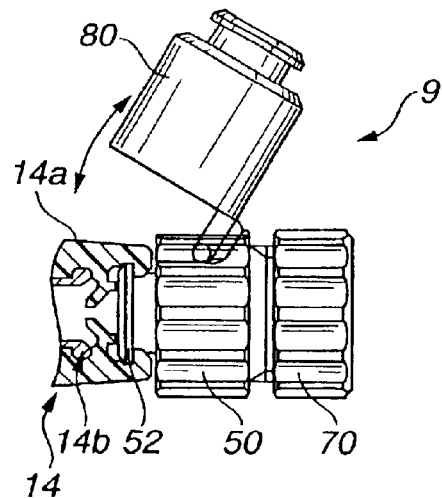
FIG. 17A illustrates a state in which the adaptor for endoscope forceps opening is mounted on the forceps plug.

First, the mounting protrusion 52 of the adaptor linking member 50 constituting the adaptor 9 is introduced into the forceps plug 14a and arranged therein, as shown in FIG. 17A. As a result, the adaptor 9 is provided integrally with a forceps plug 14a mounted on a forceps socket 14b constituting the treatment tool insertion opening 14.

In this state, the shape detection probe 1 is passed via the adaptor 9 to the prescribed position in the treatment tool passage channel 15. Once the distal end of shape detection probe 1 has been confirmed to reach the prescribed position of endoscope 3, the pressing member 70 is rotated and advanced as shown by the broken arrow line in FIG. 17B to assume a tightened state. As a result, the treatment tool integration member 60 is elastically deformed, the inner peripheral surface of the through hole for fixing 61 is brought in intimate contact with the periphery of shape detection probe 1, and the adaptor 9 and shape detection probe 1 assume an integrated state.

Figure 17B:
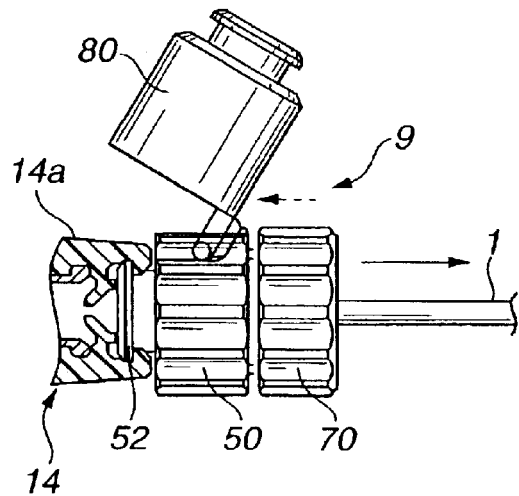
FIG. 17B illustrates a state in which the treatment tool is passed via the adaptor for endoscope forceps opening and the pressing member is tightened.
Figure 17C:
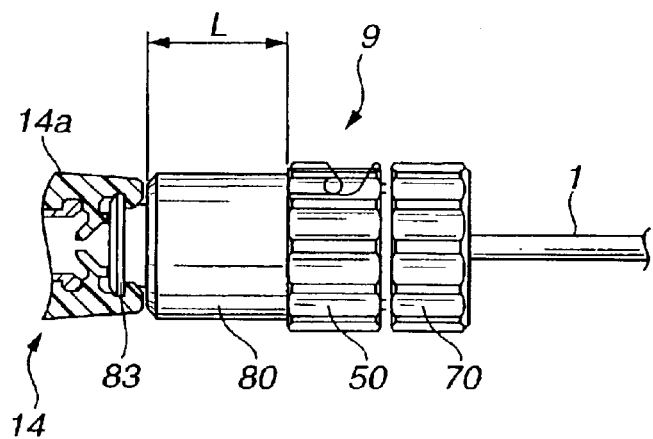
FIG. 17C illustrates a state in which the treatment tool position changing member is arranged on the front surface of the adaptor linking member.

The adaptor 9 is then moved in the direction shown by a solid arrow line in FIG. 17B. The mounting protrusion 52 is then detached from the forceps plug 14a, and the treatment tool position changing member 80 is rotated and arranged on the front side of the reference surface on the distal end side of adaptor linking member 50. The mounting protrusion 83 of treatment tool position changing member 80 is thereafter introduced into the forceps plug 14a and arranged therein, as shown in FIG. 17C.

As a result, the position of the reference surface on the distal end side of adaptor linking member 50 constituting the adaptor 9 arranged at the end surface of forceps plug 14a is pulled back for the L dimension from the end surface of forceps plug 14a. In other words, the distal end of the shape detection probe 1 integrated with the adaptor 9 is pulled back by the L dimension from the prescribed position of endoscope 3 and the arranged state is assumed.

In this state, the insertion portion 11 of the endoscope 3 is inserted into a body cavity, for example, via the anus. At this time, even if the operation is conducted so as to twist the insertion portion 11 or bend the insertion portion curved section 11a, since the shape detection probe 1 is integrated with the adaptor 9, the insertion portion 11 is prevented from moving inside the treatment tool passage channel 15. Therefore, the operator can concentrate in the insertion operation.

Thus, constructing the adaptor by providing a treatment tool integration member and pressing member at the adaptor linking member that can be detachably attached to the endoscope forceps opening makes it possible to integrally fix the adaptor and treatment tool by tightening the pressing member and elastically deforming the treatment tool integration member.

As a result, the treatment tool passed into the treatment tool passage channel is integrally held by the adaptor and movement of the treatment tool inside the treatment tool passage channel is reliably prevented. Therefore, when the endoscope insertion portion is operated in a state in which the treatment tool is arranged inside the treatment tool passage channel, the operator can give the undivided attention to the operation of the endoscope insertion portion, without bothering about holding of the treatment tool.

On the other hand, if an operation is conducted when a treatment tool, for example, forceps for biopsy, that was passed through and arranged in the treatment tool passage channel 15, is protruded when necessary for the prescribed amount from the endoscope distal end surface, the mounting protrusion 83 of the treatment tool position changing member 80 constituting the adaptor 9 is fit and arranged in advance in the forceps plug 14a provided in the treatment tool insertion opening 14, as shown in FIG. 17C.

In other words, the adaptor 9, in which the treatment tool position changing member 80 is arranged on the front side of the reference surface on the distal end side of adaptor linking member 50, is provided integrally with the forceps plug 14a. The forceps for biopsy are then passed through the adaptor 9 to the prescribed position in the treatment tool passage channel and the treatment tool integration member 60 is elastically deformed by rotating the pressing member 70. As a result, a state is assumed in which the adaptor 9 and forceps for biopsy are integrated.

An endoscope insertion portion 11 is then inserted into a body cavity, for example, through the mouth and the endoscope distal end surface is positioned opposite the observation zone at the prescribed distance therefrom. If necessary, the mounting protrusion 83 is then detached from the forceps plug 14a, the treatment tool position changing member 80 is detached by rotation from the front surface of adaptor linking member 50, and the mounting protrusion 52 of adaptor linking member 50 is fit and arranged in the forceps plug 14a.

As a result, the distal end of forceps for biopsy which are integrated with the adaptor 9 is moved for the L dimension to the distal end side. Thus, the distal end of the biopsy forceps is protruded for the prescribed distance and tissue sampling is conducted.

The amount of treatment tool pull-back or protrusion can be set to a desired value by appropriately setting the "L" dimension of the treatment tool position changing member 80.

Thus, with a configuration in which the treatment tool position changing member can be appropriately arranged on the front side of the reference surface on the distal end side of the adaptor linking member constituting the adaptor, by selecting whether the treatment tool position changing member is to be arranged on the front surface side of the adaptor linking member, mounting the adaptor on the endoscope forceps opening, and integrally fixing the treatment tool to the adaptor, it is possible to detach the treatment tool position changing member from the front surface side of the adaptor linking member or arrange it thereon, thereby making it possible to conduct a protrusion operation, in which the treatment tool is protruded for the prescribed amount, or a pull-back operation, in which the treatment tool is pulled back for the prescribed amount, in two steps.

In the present embodiment a configuration is described in which the treatment tool position changing member is rotatably installed on the adaptor linking member. However, the pull-back or protrusion amount can be changed in three or more steps by forming a plurality of treatment tool position changing members that differ by the L dimension and employing a configuration in which they can be superposed. In this case, the treatment tool position changing members that differ by the L dimension are mounted on the adaptor linking member, for example, with a string-shaped member. As a result, if necessary, the adjustment of the pull-back amount or protrusion amount is easily conducted by appropriately combining and superposing a plurality of treatment tool position changing members.

In the above-described embodiment of the adaptor, a configuration is used in which when the treatment tool pull-back or protrusion amount is changed, the treatment tool position changing member 80 constituting the adaptor 9 mounted on the forceps plug 14a, if necessary, is mounted on the front side of the reference surface on the distal end side of adaptor linking member 50 or detached from the front side. However, an adaptor 9A may be also constructed such as to conduct changing of the treatment tool pull-back amount or protrusion amount by causing the treatment tool position changing member to execute sliding movement in the longitudinal axis direction.

Figure 18:
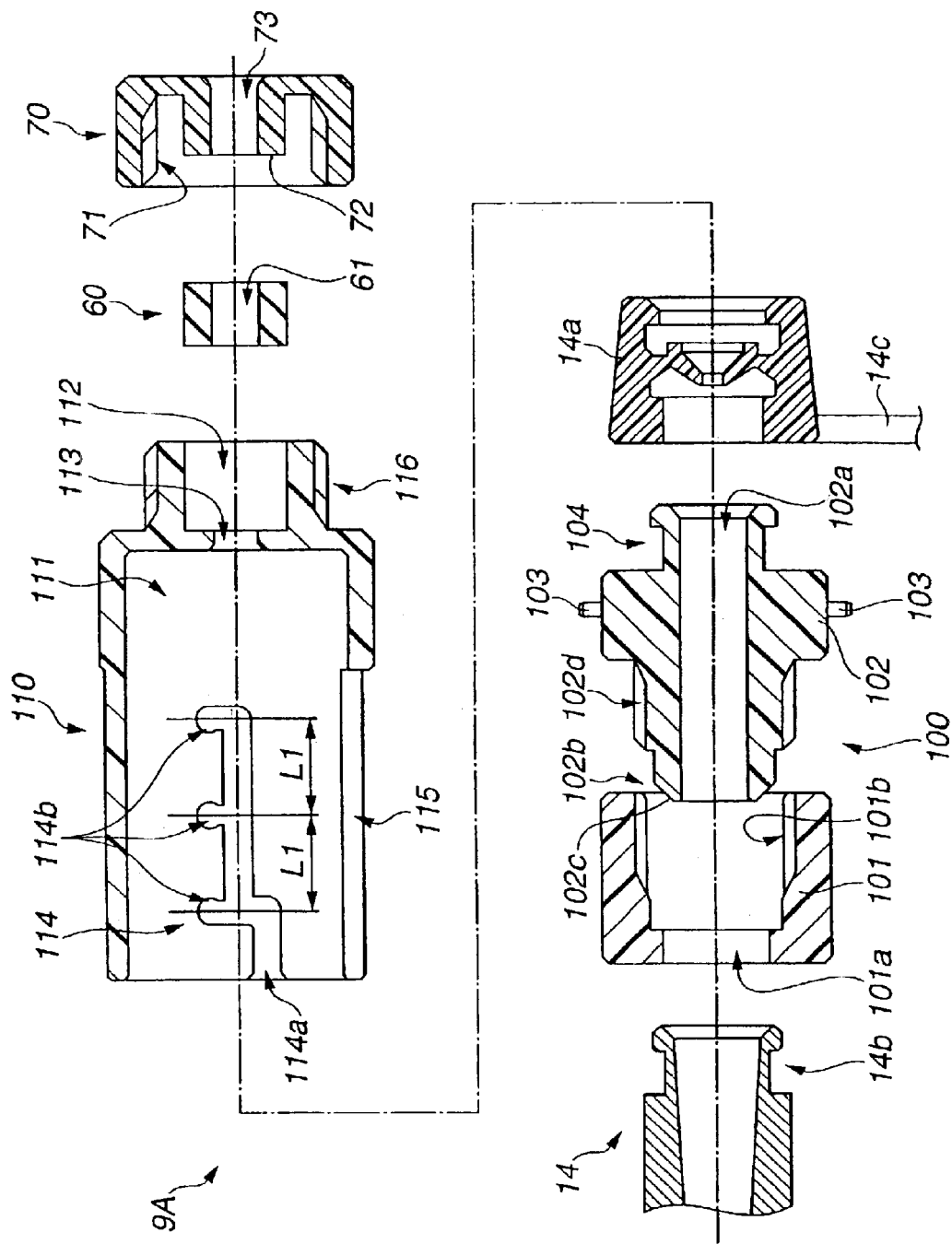
FIG. 18 illustrates structural components of the adaptor for endoscope forceps opening.

The adaptor 9A with such a configuration is shown in FIG. 18. This adaptor 9A is composed of an adaptor linking member 100, a treatment tool position changing member 110 having a tubular shape, the treatment tool integration member 60 having a tubular shape, and a pressing member 70 with the internal thread portion 71 formed therein. The adaptor linking member 100 is formed, for example, of a resin material and mounted on the forceps socket 14b so that it can be attached thereto and detached therefrom. The treatment tool position changing member 110 is formed of a resin material and is arranged so that it is free to slide on the outer peripheral surface side of the adaptor linking member 100.

The adaptor linking member 100 is composed of a first socket fixing member 101 in which a through hole 101a for passing the distal end portion of the forceps socket 14b is formed in axial direction in the almost central portion thereof and a second socket fixing member 102 in which a through hole 102a for passing a treatment tool is formed in axial direction in the almost central portion thereof. The first socket fixing member 101 has an almost U-like cross-sectional shape, with an internal thread portion 101b being formed on the inner peripheral surface of the recess. The second socket fixing member 102 has a substantially cruciform cross section.

A contact surface 102c of a distal end side portion 102b abutting on the proximal surface of the forceps socket 14b, and an external thread portion 102d positioned in the side portion of an intermediate zone for engagement with the internal thread portion 101b are provided on the projection on the distal end side of the second socket fixing member 102.

Furthermore, a pair of positioning pins 103 are provided in a protruding condition in the prescribed positions on the outer peripheral surface of a large-diameter portion of the second socket fixing member 102. A plug mounting portion 104 of the same shape as the end portion of the forceps socket 14b for mounting the forceps plug 14a is provided on the proximal end of the second socket fixing member 102.

The treatment tool position changing member 110 has a thin elongated almost tubular shape. The treatment tool position changing member 110 comprises a first recess 111 and a second recess 112. The first recess 111 and second recess 112 communicate via a through hole 113 for passing a treatment tool. The adaptor linking member 100 composed of the integrated first socket fixing member 101 and second socket fixing member 102 is arranged in the first recess 111. The treatment tool integration member 60 is arranged in the second recess 112.

A pair of motion-control grooves 114 in which the positioning pins 103 are to be arranged are formed so as to be positioned opposite each other in the side peripheral surface of the first recess 111 of the treatment tool position changing member 110.

The motion-control groove 114 comprises a motion groove 114a and a plurality of fitting grooves 114b. Arranging the positioning pin 103 in the motion groove 114a causes the treatment tool position changing member 110 to slide with respect to the axial direction of the adaptor linking member 100. On the other hand, arranging the positioning pin 103 in the fitting groove 114b controls the position of the treatment tool position changing member 110 so that the prescribed position is assumed. The fitting groove 114b of the present embodiment is composed, for example, of three fitting grooves, first fitting groove, second fitting groove, and third fitting groove in a regular order from the open side of the first recess 111. Spacing between the fitting grooves is set to the "L1" dimension.

A reference numeral 115 stands for a notched portion communicated with the first recess 111 where the linking portion 14c of the forceps plug 14a is positioned. This notched portion 115 is formed in a position at an angle of about 90 degrees with respect to the tangential direction from one motion-control groove 114. A reference symbol 116 stands for an external thread portion which is to be engaged with the internal thread portion 71 of the pressing member 70. All other structural features are the same as those of the adaptor 9. The same components are assigned with the same reference symbols and explanation thereof is omitted.

The installation of adaptor 9A will be described below.

Figure 19A:
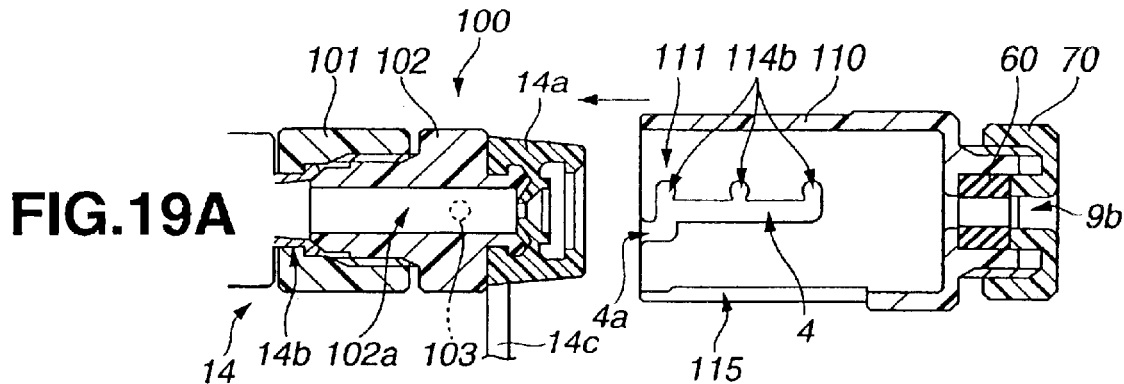
FIG. 19A illustrates a state prior to installation of the adaptor for endoscope forceps opening.

Different from the adaptor 9, the adaptor 9A of the present embodiment is constructed integrally with the treatment tool insertion opening 14. Therefore, first, the adaptor linking member 100 is mounted on the forceps socket 14b, as shown in FIG. 19A. On the other hand, the treatment tool integration member 60 is arranged inside the recess 112 of the treatment tool position changing member 110. Then, in this state, the internal thread portion 71 of the pressing member 70 is engaged with the external thread portion 116 of the treatment tool position changing member 110, and the treatment tool position changing member 110, treatment tool integration member 60, and pressing member 70 are integrated.

When the adaptor linking member 100 is mounted on the forceps socket 14b, the distal end portion of forceps socket 14b is passed through the through hole 101a of the first socket fixing member 101, and the distal end portion of the forceps socket 14b is arranged on the bottom surface of the first socket fixing member 101. Then, the external thread portion 102d of the second socket fixing member 102 is engaged with the internal thread portion 101b of the first socket fixing member 101. As a result, the contact surface 102c of the side portion 102b on the distal end abuts on the forceps socket 14b and a fully engaged state is assumed.

As a consequence, the adaptor linking member 100 composed of the first socket fixing member 101 and second socket fixing member 102 is fixed to the forceps socket 14b. Further, the forceps plug 14a is arranged on the plug mounting portion 104.

Then, the treatment tool position changing member 110 with the treatment tool integration member 60 and pressing member 70 integrated therewith is advanced toward the adaptor linking member 100, as shown by an arrow. The first recess 111 is then arranged on the outer peripheral side of the forceps plug 14a and second socket fixing member 102. At this time, the positioning pin 103 is arranged inside the motion groove 114a and the linking portion 14c is arranged in the notched portion 115.

Figure 19B:
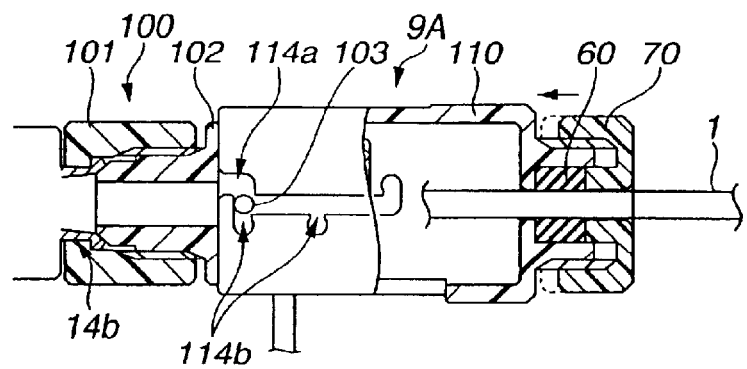
FIG. 19B illustrates the adaptor for endoscope forceps opening installed on the forceps socket.

In this state, the treatment tool position changing member 110 is caused to slide along the motion groove 114a, with the positioning pin 103 serving as a guide, and the positioning pin 103 is positioned opposite the first fitting groove 114b, as shown in FIG. 19B. The treatment tool position changing member 110 is then slightly rotated as shown by an arrow and the positioning pin 103 is arranged in the fitting groove 114b and assumes a retained state.

As a result, the adaptor 9A assumes a state in which it is mounted on the forceps socket 14b. At this time, the distal end surface of the pressing protrusion 72 of the pressing member 70 contacts the end surface of the treatment tool integration member 60. Therefore, if the insertion shape detection probe 1 is inserted into the treatment tool passing hole 9b of the adaptor 9, the insertion shape detection probe 1 smoothly passes through the through hole for fixing 61 constituting the treatment tool passing hole 9b.

The pressing member 70 is then rotated and further tightened as shown by an arrow in FIG. 19B. The treatment tool integration member 60 is thereby elastically deformed in the same manner as in the first embodiment. As a result, the inner peripheral surface of the through hole for fixing 61 is brought in intimate contact with the periphery of the insertion shape detection probe 1 that is inserted into the treatment tool passing hole 9b. Thus, the insertion shape detection probe 1 and adaptor 9A assume an integrated state and positioning can be reliably conducted.

Figure 19C:
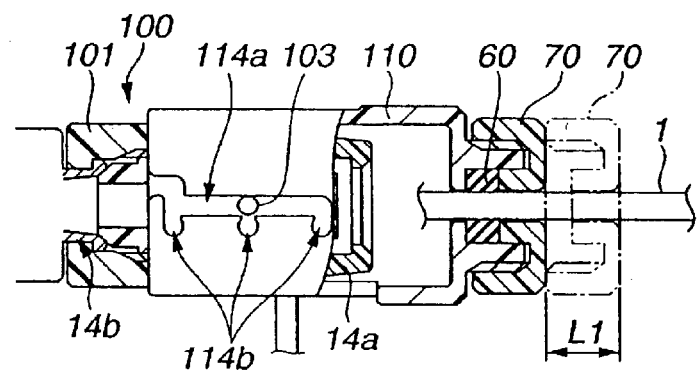
FIG. 19C illustrates a state in which the treatment tool is one-step moved from the position shown in FIG. 19B to the distal end side.

In this state, the treatment tool position changing member 110 is again rotated and moved so that the positioning pin 103 is transferred from the fitting groove 114b to the motion groove 114a. The treatment tool position changing member 110 is then caused to slide and pushed into the treatment tool insertion opening 14, thereby disposing the positioning pin 103 opposite the second insertion groove 114 of the treatment tool position changing member 110, as shown in FIG. 19C. As a result, the proximal end surface of the pressing member 70 assumes a state to which it was moved by the dimension of L1.

If then the treatment tool position changing member 110 is slightly moved and rotated and the positioning pin 103 is arranged in the second fitting groove 114*b*, the proximal end surface of the pressing member 70 is retained in the state to which it was moved by the dimension of L1. At this time, the insertion shape detection probe 1 that has been integrally fixed by the treatment tool integration member 60 which is integrated with the treatment tool position changing member 110 is also moved through L1 in the distal end direction.

Figure 19D:
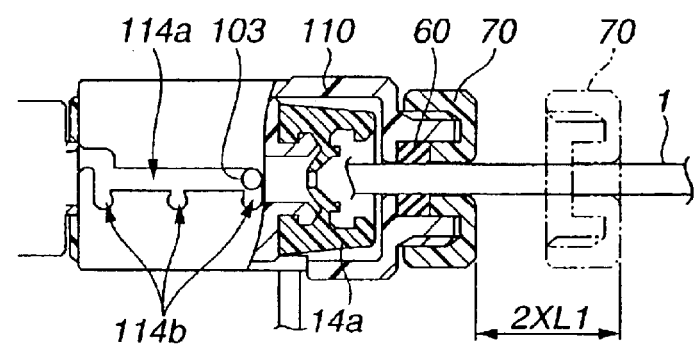
FIG. 19D illustrates a state in which the treatment tool is two-step moved from the position shown in FIG. 19B to the distal end side.

When the treatment tool position changing member 110 is caused to slide and pushed into the treatment tool insertion opening 14, the positioning pin 103 passes through the second fitting groove 114*b* of the treatment tool position changing member 110 and is placed opposite the third fitting groove 114*b*. As a result, a state is assumed in which the proximal end surface of the pressing member 70 was moved through doubled dimension of L1, as shown in FIG. 19D.

If then the treatment tool position changing member 110 is slightly rotated and moved and the positioning pin 103 is arranged in the third fitting groove 114*b*, the proximal end surface of the pressing member 70 is retained in the state to which it was moved through doubled dimension of L1. At this time, the insertion shape detection probe 1, that was integrally fixed by the treatment tool integration member 60 which is integrated with the treatment tool position changing member 110, also moves through doubled dimension of L1 in the distal end direction.

In the present embodiment, a movement example is described in which the positioning pin is first arranged in the first fitting groove and the treatment tool is pushed forward in the distal end direction in two steps. However, the positioning pin may be initially arranged in the third fitting groove and the treatment tool may be moved in two steps in the proximal end direction, or the positioning pin may be initially arranged in the second fitting groove and the treatment tool may be moved back and forth, one step in each direction.

Further, in the present embodiment, three fitting grooves 114*b* are formed in the axial direction. However, the number of fitting grooves 114*b* is not limited to three and may be more or less than that.

Furthermore, the movement amount of the treatment tool in the distal or proximal end direction can be set to the desired value by appropriately setting the L1 dimension which is the spacing between the fitting grooves.

Thus, the adaptor is constructed such that the treatment tool position changing member is free to slide in the axial direction by integrating the treatment tool position changing member, which has the treatment tool integration member and pressing member integrated therewith, and the adaptor linking member that can be mounted on the endoscope forceps opening so as to be attached thereto and detached therefrom. As a result, it is possible to move the treatment tool through the prescribed distance in the desired direction by causing a sliding movement of the treatment tool position changing member with respect to the adaptor linking member.

The treatment tool protrusion or pull-back operation is thus conducted by a simple operation of causing a sliding movement of the treatment tool position changing member in the axial direction. Other functions and effects are identical to those of the above-described embodiment.

Having described the preferred embodiments of the invention referring to the accompanying drawings, it should be understood that the present invention is not limited to those precise embodiments, and thus various changes and modifications thereof could be made by one skilled in the art without departing from the spirit or scope of the invention as defined in the appended claims.

What is claimed is:

1. An adaptor for endoscope forceps opening comprises:
an adaptor linking member that can be detachably attached to the endoscope forceps opening communicated with the treatment tool passage channel through which the treatment tool is to be passed;
a treatment tool integration member which is in tight contact with and fixed to part of the treatment tool protruding from said endoscope forceps opening; and
a treatment tool position changing member for changing stepwise, together with the treatment tool integration member, the insertion position of the treatment tool in a state in which said treatment tool integration member is in tight contact therewith.

2. An adaptor for endoscope forceps opening comprises:
a tubular adaptor linking member having a mounting portion that can be detachably attached to an endoscope plug provided in the endoscope forceps opening through which the treatment tool is to be passed;
a treatment tool integration member having a tubular shape and elastic properties and arranged in a prescribed position of the adaptor linking member,
a pressing member arranged so that it is free to advance and retreat with respect to said adaptor linking member and used to apply a pressure with a prescribed force to said treatment tool integration member for elastic deformation thereof, thereby causing the treatment tool integration member to be brought in intimate contact with and fixed to part of said treatment tool; and
a treatment tool position changing member which has a tubular shape, comprises a mounting portion that can be detachably attached to said forceps plug and a notched portion communicated with the axial through hole, and is arranged so that it can be detachably attached to the distal end side of said adaptor linking member.

3. An adaptor for endoscope forceps opening comprises:
an adaptor linking member which can be detachably attached to a forceps socket constituting the endoscope forceps opening through which the treatment tool is to be passed and is composed of a first socket fixing member arranged on the outer peripheral side of the forceps socket and a second socket fixing member in which a positioning pin is provided in a protruding condition from a prescribed position on the outer peripheral surface which is integrally fixed to the first socket fixing member in a state where the second socket fixing member is abutted against the distal end side of said forceps socket;
a treatment tool position changing member which is arranged so as to be free to advance and retreat with respect to said adaptor linking member and has formed therein a motion-control groove that can move along said positioning pin and can be retained by the positioning pin;

a treatment tool integration member having a tubular shape and elastic properties and arranged in a prescribed position of the treatment tool position changing member; and a pressing member arranged so as to be free to advance and retreat with respect to said tool position changing member and used to apply a pressure with a prescribed force to said treatment tool integration member for elastic deformation thereof, thereby causing the treatment tool integration member to be brought in intimate contact with and fixed to part of said treatment tool.

4. The adaptor for endoscope forceps opening according to claim 1, wherein said treatment tool position changing member is provided rotatably on said adaptor linking member.

5. An adaptor for an endoscope forceps opening, the adaptor comprising:

an adaptor linking member detachably attached to the endoscope forceps opening and in communication with a treatment tool passage channel through which a treatment tool is to be passed;

a treatment tool integration member which engages with a portion of the treatment tool protruding from the endoscope forceps opening to fix a position of the treatment tool relative to a treatment tool position changing member; and the treatment tool position changing member for changing the insertion position of the treatment tool while said treatment tool integration member is engaged with the treatment tool.

* * * * *